United States Patent [19]
Nishikawa et al.

[11] Patent Number: 5,869,732
[45] Date of Patent: Feb. 9, 1999

[54] PROCESS FOR PRODUCING TRICYANOETHYLATED PENTAERYTHRITOL

[75] Inventors: Satoshi Nishikawa, Shiga-gun; Shinji Bessho, Suita, both of Japan

[73] Assignees: Sunstar Giken Kabushiki Kaisha, Takatsuki, Japan; Uni-Sunstar B.V., Amsterdam, Netherlands

[21] Appl. No.: 889,937

[22] Filed: Jul. 10, 1997

[51] Int. Cl.$^6$ ................................................ C07C 255/00
[52] U.S. Cl. ........................................... 558/447; 558/450
[58] Field of Search ..................... 558/447, 450

[56] References Cited

U.S. PATENT DOCUMENTS

| | | | |
|---|---|---|---|
| 2,383,443 | 8/1945 | Bruson | 558/447 |
| 2,407,607 | 6/1946 | Bruson, II | 558/447 |
| 2,437,905 | 3/1948 | Bruson, III | 558/447 |

FOREIGN PATENT DOCUMENTS

| | | | |
|---|---|---|---|
| 0674307 | 11/1963 | Canada | 558/450 |
| 46-55502 | 3/1973 | Japan | 558/450 |

*Primary Examiner*—Floyd D. Higel
*Attorney, Agent, or Firm*—Jacobson, Price, Holman & Stern, PLLC

[57] ABSTRACT

An imporved process for producing tricyanoethylated pentaerythritol by selectively cyanoethylating only three hydroxy groups of pentaerythritol in a high yield such as 90 to 95%, involves reacting one mole of pentaerythritol with three mole of acrylonitrile by Micheal Addition Reaction in an alkaline aqueous solution in coexistence with an extraction solvent. The tricyanoethylated pentaerythritol has a high purity and is useful for production of a high dielectric polymer.

4 Claims, No Drawings

PROCESS FOR PRODUCING TRICYANOETHYLATED PENTAERYTHRITOL

FIELD OF INVENTION

This invention relates to a process for producing a tricyanoethylated pentaerythritol, which is useful as a material for producing a high dielectric polymer. More particularly, it relates to a process for producing a tricyanoethylated pentaerythritol by selectively cyanoethylating only three hydroxy groups of pentaerythritol in a very high yield such as 90 to 95%.

BACKGROUND OF THE INVENTION

A tricyanoethylated pentaerythritol of the formula:

$$HOCH_2C(CH_2OCH_2CH_2CN)_3$$

has usually been produced by reacting 1 mole of pentaerythritol of the formula: $C(CH_2OH)_4$ with 3 moles of acrylonitrile, for example, by Michael Addition Reaction in an alkaline aqueous medium. The tricyanoethylated pentaerythritol is usually used for producing a high dielectric polymer containing a cyano group, which comprises monoesterifying the tricyanoethylated pentaerythritol with acrylic acid or methacrylic acid and homopolymerizing or copolymerizing one or more of the resulting cyanoethyl group-containing (meth)acrylic ester monomers optionally with other copolymerizable monomer, or alternatively graft-polymerizing the cyanoethyl group-containing (meth) acrylic ester monomers with other polymer (cf. JP-A-5-140234, JP-A-5-140235, JP-A-6-263825, and JP-8-134149=U.S. Ser. No. 08/558,776 filed on Nov. 15, 1995, and now U.S. Pat. No. 5,777,038). The high dielectric polymer is usually used as an organic electronic material, such as a binder for an organic dispersion-type electroluminescense device or a dielectric material for a film condenser (cf. JP-A-6-336506, and JP-A-8-134149=U.S. Ser. No. 08/558, 776, and now U.S. Pat. No. 5,777,638).

The tricyanoethylated pentaerythritol is usually produced by Michael Addition Reaction of pentaerythritol and acrylonitrile as mentioned above, more specifically, by subjecting the starting materials to Michael Addition Reaction in an alkaline aqueous solution, extracting the produced tricyanoethylated pentaerythritol with an appropriate solvent (e.g. methylene chloride), separating the phase of the extraction solvent from the reaction system, neutralizing the extract and then washing it with water, or alternatively washing the extract with water until it becomes neutral, and finally distilling the extract thus treated.

However, according to the conventional method, there are produced various by-products such as mono-, di- and/or tetra-cyanoethylated products in addition to the desired tricyanoethylated pentaerythritol, which cause lowering of the yield and purity of the desired tricyanoethylated pentaerythritol. Even though the reaction is carried out by using the most suitable molar ratio of the starting pentaerythritol and acrylonitrile at the best reaction conditions, the obtained tricyanoethylated pentaerythritol has a low purity, for example, a purity of upto 50 to 55%. Besides, since tricyanoethylated pentaerythritol has a high molecular weight and a high boiling point, it is very difficult to purify by a conventional method such as distillation, and hence, in order to obtain a product having a purity of 90% or more, it is necessary to treat the product with a column filled with an adsorbent such as silica gel, which is disadvantageous in view of a high cost.

BRIEF SUMMARY OF THE INVENTION

The present inventors have intensively studied to find an improved process for the production of tricyanoethylated pentaerythritol in order to enhance the purity of the product more than 90%, more preferably more than 95%, and have found that when the Michael Addition Reaction is carried out in an alkaline aqueous solution in coexistence with an extraction solvent, the cyanoethylating reaction proceeds selectively only for three hydroxy groups and thereby the production of undesirable by-products is significantly inhibited to give the desired tricyanoethylated pentaerythritol at a high purity of 90 to 95% or higher, which is advantageous in view of lowering the production cost and also in view of improving the properties of the product.

Thus, an object of the invention is to provide an improved method for the production of tricyanoethylated pentaerythritol with a high selectivity. Another object of the invention is to provide a tricyanoethylated pentaerythritol having a high purity of 90 to 95% or higher, which is useful as a material for a high dielectric polymer. These and other objects of the invention will be apparent to those skilled in the art from the following description.

DETAILED DESCRIPTION OF THE INVENTION

The process for the production of tricyanoethylated pentaerythritol (occassionally abbreviated as "3CE-PET") of the formula: $HOCH_2C(CH_2OCH_2CH_2CN)_3$ of this invention comprises reacting 1 mole of pentaerythritol (occasionally abbreviated as "PET") of the formula: $C(CH_2OH)_4$ with 3 moles of acrylonitrile (occasionally abbreviated as "AN") by Michael Addition Reaction in an alkaline aqueous solution in coexistence with a solvent for extracting the desired "3CE-PET".

It is not clear so the reason why the method of this invention can give the desired product in such a high purity, but it is assumed as follows.

In the conventional method, even after the cyanoethylation of three hydroxy groups of the starting pentaerythritol is completed, the reaction proceeds further to produce partly a tetracyanoethylated by-product. On the contrary, according to the process of the present invention wherein the reaction proceeds in coexistence with an extraction solvent, the reaction system is separated into two layers of the extraction solvent phase and the aqueous phase throughout the whole reaction from the initiation to the final stage thereof because both phases are immiscible with each other. In such a reaction system, the monocyanoethylated and dicyanoethylated products are contained in the aqueous phase owing to the remaining hydrophilic OH groups (three or two OH groups), and the tricyanoethylated product and tetracyanoethylated product (if any) are easily dissolved in the extraction solvent phase. The Michael Addition Reaction is carried out in the presence of an alkaline catalyst, and hence, the cyanoethylating reaction proceeds only in the aqueous phase because the alkaline catalyst (e.g. NaOH) is dissolved only in the aqueous solution. Thus, according to the process of the present invention, when the tricyanoethylated product is produced in the aqueous phase, it moves immediately into the extraction solvent phase and hence it is no more cyanoethylated.

The alkaline aqueous solution to be used as a reaction medium in Michael Addition Reaction of the present invention includes, for example, a 0.1–10% aqueous solution of a conventional alkaline catalyst such as caustic alkalis (e.g. NaOH, KOH, LiOH) or organic bases (e.g. quaternary ammonium compounds such as benzyltrimethylammonium hydroxide, tetramethylammonium hydroxide, etc.), a particularly preferable aqueous medium is a 1–5% aqueous solution of a caustic alkali.

The extraction solvent to be coexistent in the alkaline aqueous solution is a solvent which can dissolve well the produced 3CE-PET and is immiscible with water and includes, for example, a chlorinated hydrocarbon having 1 to 5 carbon atoms (e.g. methylene chloride, ethylene dichloride, 1,1,1-trichloroethane, chloroform), and an aromatic hydrocarbon (e.g. toluene), which may be used alone or in combination of two or more thereof. The solvent is usually used at a ratio of the alkaline aqueous solution: the solvent being in the range of 20:1 to 1:10 by weight, more preferably 10:1 to 1:10 by weight. When the solvent is used at less than the lower ratio, that is, less than 1 part by weight to 20 parts by weight of the alkaline aqueous solution, the produced 3CE-PET has disadvantageously less purity, and on the other hand, when the solvent is used at a larger ratio than the above, that is, more than 10 parts by weight to 1 part by weight of the alkaline aqueous solution, it results disadvantageously in less efficiency in charging materials into the reaction vessel, in other words, in less yield of the product per the reaction vessel, and further in high cost for distilling off the solvent after reaction.

The process for producing 3CE-PET of the present invention is more specifically carried out in the following manner.

One mole of PET is reacted with 3 moles, or somewhat more amount, of AN in a mixture of an alkaline aqueous solution and an extraction solvent at the ratio of 20:1 to 1:10 by weight and the mixture is subjected to Michael Addition Reaction under the conditions of: a temperature of 20° C. to 60° C. for 1 to 48 hours, allowing to stand the reaction mixture until the reaction mixture is separated clearly into two phases, removing the aqueous phase, washing well the extraction solvent phase with water, dehydrating, and removing the extraction solvent by a conventional method, for example, by distillation under reduced pressure, by which the desired 3CE-PET is obtained in a highly pure form, such as in 90 to 95% purity.

The tricyanoethylated pentaerythritol obtained by the process of the present invention can be used for the production of a high dielectric polymer by the following method.

The tricyanoethylated pentaerythritol is monoesterified with a radical polymerizable monocarboxylic acid (e.g. acrylic acid or methacrylic acid) or with a radical polymerizable dicarboxylic acid (e.g. maleic acid, fumaric acid, or itaconic acid) to give a cyanoethyl group-containing radical polymerizable monomer, followed by subjecting said cyanoethyl group-containing monomer to homopolymerization, copolymerization or graft-polymerization to give the desired cyano group-containing high dielectric polymer. The copolymerization may be done by using two or more kinds of the cyanoethyl group-containing radical polymerizable monomer or alternatively by copolymerizing a cyanoethyl group-containing radical polymerizable monomer with other copolymerizable monomer (cf. JP-A-5-140234, JP-A-5-140235, and JP-A-6-263825), or alternatively graft-polymerizing a cyanoethyl group-containing radical polymerizable monomer with other polymers (cf. JP-A-8-134149=U.S. Ser. No. 08/558,776, now U.S. Pat. No. 5,777,308).

The high dielectric polymer thus obtained is useful as an organic electronic material, such as a binder for an organic dispersion-type electroluminescense device or a dielectric material for a film condenser, in view of the high dielectric properties. Besides, the high dielectric polymer is also useful as a binder resin or a solid electrolytic material for electrodes (e.g. lithium ion secondary battery) in view of the ion conductivity thereof. It is also useful as a solid electrolytic material for an electrocromic device.

The tricyanoethylated pentaerythritol obtained by the process of the present invention has a high purity, but is still contaminated with a small amount of mono- and/or di-cyanoethylated product, which may cause disadvantageous gelation due to esterification or polymerization thereof during usage. The contamination is believed to be due to the fact that the concentration of 3CE-PET in the phase of the extraction solvent is increased with progression of the reaction, whereby the resulting mixture of the extraction solvent and 3CE-PET becomes a solvent for mono- and/or di-cyanoethylated products and then said mono- and/or di-cyanoethylated products are dissolved in the extraction solvent phase, notwithstanding those mono- and/or di-cyanoethylated products are hardly dissolved in the extraction solvent per se. In order to prevent such a disadvantageous phenomenon, it can be considered to increase the volume of the extraction solvent to be used, but it results disadvantageously in a high cost.

For the purpose of preventing the undesirable increase of contamination of mono- and/or di-cyanoethylated product in the extraction solvent phase, the extraction solve can optionally be blended with a small amount of a solvent in which the mono- and di-cyanoethylated pentaerythritol has less solubility, for example, with an alipahatic or alicyclic hydrocarbon solvent (e.g. n-hexane, or cyclohexane).

The present invention is illustrated by the following Examples and Reference Examples, but should not be construed to be limited thereto.

EXAMPLE 1

A three-necked flask is charged with a 2% NaOH aqueous solution (204 g), PET (68.08 g, 0.5 mole) and methylene chloride (136 ml, 181.7 g), and to the mixture is added dropwise AN (84.9 g, 1.6 mole) with vigorous stirring under reflux temperature (inner temperature: 35°–40° C.) over a period of 4 hours. The mixture is further stirred at the same temperature for 3 hours.

After the reaction, the reaction mixture is allowed to stand to separate into two layers (the upper layer: an aqueous phase, the lower layer: a methylene chloride phase). The aqueous phase is removed, and the methylene chloride phase is washed well with water until it is no longer alkaline. Thereafter, the mixture is dehydrated with a rotary pump and methylene chloride is distilled off under reduced pressure.

The product is subjected to gas chromatography (GC) to determine the purity of 3CE-PET under the following conditions:

Column: Capillary TC-1 (manufactured by Shimadzu Corporation)

Injection: 300° C.

Temperature of column: 310° C.

Sample solution: A 2% methyl ethyl ketone solution

Based on the GC chart thus obtained, the purity of CE-PET was calculated. As a result, it showed the following data:

Content of 3CE-PET: 95.3%

Content of tetracyanoethylated product: 4.7%

REFERENCE EXAMPLE 1

A three-necked flask is charged with a 2% NaOH aqueous solution (90 g) and PET (68.08 g, 0.5 mole), and to the mixture is added dropwise AN (92.99 g, 1.7 mole) with vigorous stirring at a temperature of 40°–45° C. over a period of 3 hours. The mixture is further stirred at the same temperature for 3 hours.

The reaction mixture is extracted with methylene chloride to isolate 3CE-PET, and the methylene chloride phase is washed well with water until it is no longer alkaline. Thereafter, the mixture is dehydrated with a rotary pump and methylene chloride is distilled off under reduced pressure.

In the same manner as described in Example 1, the purity of 3CE-PET was measured. As a result, it showed the following data:

Content of 3CE-PET: 54.1%

Content of tetracyanoethylated product: 45.9%

Thus, in this reference example, the cyanoethylation proceeds partly even after 3CE-PET is produced to give a tetracyanoethylated product.

EXPERIMENT 1

The 3CE-PETs obtained in Example 1 and Reference Example 1 were monoesterified with methacrylic acid in a usual manner, and the products were subjected to gas chromatography, and the contents of the products were analysed with the resulting GC charts. As a result, there were obtained the following data.

|  | 3CE-PET of Example 1 | 3CE-PET of Ref. Ex. 1 |
|---|---|---|
| Momoesterified product of 3CE-PET | 94.4% | 59.9% |
| Remaining tetracyano-ethylated product | 3.3% | 32.8% |
| Other contaminants | 2.3% | 7.3% |

EFFECTS OF THE INVENTION

The process of the present invention has the following advantages.

(1) The desired 3CE-PET can be obtained in a high purity such as 90–95% or more, because the produced 3CE-PET moves immediately to the extraction solvent phase and thereby tetracyanoethylation is effectively inhibited whereas while it can not be prevented by the conventional methods and further because undesirable hydrolysis of —CN to —COOH can be prevented.

(2) Owing to the coexistence of an extraction solvent in the reaction system, the step for extraction of the product can be omitted, and further the reaction can be carried out under the reflux temperature of the extraction solvent and hence the reaction temperature can easily be controlled.

(3) The desired product 3CE-PET has extremely low contamination with mono- and/or di-cyanoethylated products, and hence, when it is monoesterified with acrylic or methacrylic acid for obtaining a high dielectric polymer, there is no gelation, and the polymer product has superior dielectric properties.

(4) Owing to the establishment of the process for production of 3CE-PET with high selectivity of the degree of cyanoethylation, it can give high effeciency in the step of the production of a high dielectric polymer, i.e., high yield of the desired polymer per the reaction vessel, which results in a low cost for the production of the desired polymer.

(5) When a high dielectric polymer is produced by homopolymerization, copolymerization or graft-polymerization of the monoesterified 3CE-PET, the desired polymer is obtained in a high yield with less gelation and further a step for purification of the polymer product can be omitted or simplified.

What is claimed is:

1. A process for the production of tricyanoethylated pentaerythritol of the formula: $HOCH_2C(CH_2OCH_2CH_2CN)_3$, which comprises reacting 1 mole of pentaerythritol of the formula: $C(CH_2OH)_4$ with 3 moles of acrylonitrile by Michael Addition Reaction in an alkaline aqueous solution in coexistence with a solvent for extracting the tricyanoethylated pentaerythritol.

2. The process according to claim 1, wherein the alkaline aqueous solution is a 0.1 to 10% caustic alkaline aqueous solution, and the extraction solvent is a chlorinated hydrocarbon having 1 to 5 carbon atoms or an aromatic hydrocarbon.

3. The process according to claim 1, wherein the alkaline aqueous solution and the extraction solvent are at a ratio of 20:1 to 1:10 by weight.

4. The process according to claim 2, wherein the alkaline aqueous solution and the extraction solvent are at a ratio of 20:1 to 1:10 by weight.

* * * * *